United States Patent
Golub et al.

(10) Patent No.: US 9,757,436 B2
(45) Date of Patent: Sep. 12, 2017

(54) ANTIMICROBIAL COMPOSITION COMPRISING PYROGENIC SILICA AND SERRATHIOPEPTIDASE AND USES THEREOF

(71) Applicant: Willingsford Limited, Hampshire (GB)

(72) Inventors: Alexandr A. Golub, Kiev (UA); Olga Biliaieva, Kiev (UA); Viacheslav V. Neshta, Zaporozhie (UA)

(73) Assignee: Willingsford Limited, Hampshire (GB)

( * ) Notice: Subject to any disclaimer, the term of this patent is extended or adjusted under 35 U.S.C. 154(b) by 162 days.

(21) Appl. No.: 14/753,641

(22) Filed: Jun. 29, 2015

(65) Prior Publication Data

US 2015/0297787 A1   Oct. 22, 2015

Related U.S. Application Data

(63) Continuation of application No. 12/668,827, filed as application No. PCT/UA2008/000041 on Jul. 11, 2008, now Pat. No. 9,302,027.

(30) Foreign Application Priority Data

Jul. 12, 2007   (UA) .................................. 200707897

(51) Int. Cl.
| | | |
|---|---|---|
| *A61K 47/00* | (2006.01) | |
| *A61K 38/48* | (2006.01) | |
| *A61K 9/00* | (2006.01) | |
| *A61K 47/02* | (2006.01) | |
| *A61L 15/18* | (2006.01) | |
| *A61L 15/38* | (2006.01) | |
| *A61L 15/44* | (2006.01) | |
| *A61L 15/46* | (2006.01) | |
| *A61L 26/00* | (2006.01) | |
| *A61K 9/16* | (2006.01) | |

(52) U.S. Cl.
CPC ........ *A61K 38/4886* (2013.01); *A61K 9/0014* (2013.01); *A61K 9/1676* (2013.01); *A61K 47/02* (2013.01); *A61L 15/18* (2013.01); *A61L 15/38* (2013.01); *A61L 15/44* (2013.01); *A61L 15/46* (2013.01); *A61L 26/0004* (2013.01); *A61L 26/0047* (2013.01); *A61L 26/0066* (2013.01); *A61L 26/0095* (2013.01); *A61L 2300/254* (2013.01); *A61L 2300/404* (2013.01); *C12Y 304/2404* (2013.01)

(58) Field of Classification Search
None
See application file for complete search history.

(56) References Cited

PUBLICATIONS

Mishchuk et al., Klin Khir. 1994;(4):21-2.*
Selan et al., Antimicrobial Agents and Chemotherapy, Dec. 1993, p. 2618-2621.*
Maheshwari et al., "Development of tetracycline-serratiopeptidase-containing periodontal gel: formulation and preliminary clinical study," AAPS Pharmscitech, 7:E 1-E10, 2006.*
ECETOC JACC Report No. 51,2006 (http://members.ecetoc.org/Documents/Document/JACC%20051.pdf).*
Schaefr and Hurd, Growth and Structure of Combustion Aerosols, Aerosol Sci. Technol. 12:876-890 (1990).
Degussa AG, Aerosil Silanes, Nummer 11 (2003).
Evonik Industries, Basic Characteristics of Aerosil Fumed Silica, Technical Bulletin 11, (2006).

* cited by examiner

*Primary Examiner* — Irene Marx
(74) *Attorney, Agent, or Firm* — James Butler

(57) ABSTRACT

Methods are provided for treatment of wounds using a complex antimicrobial sorption composition possessing the necrolytic effect for treating the purulent wounds, the trophic ulcers, the wounds, and the infiltrates with the significant necrotic and exudative components represents the silica sorbent with the immobilized drug. Pyrogenic silica is used as a siliceous sorbent, and serrathiopeptidase as a drug.

3 Claims, No Drawings

ANTIMICROBIAL COMPOSITION COMPRISING PYROGENIC SILICA AND SERRATHIOPEPTIDASE AND USES THEREOF

PRIORITY CLAIM

This Continuation Application is filed under 37 C.F.R. 1.53(b), claiming priority to U.S. patent application Ser. No. 12/668,827 filed 6 May 2010, which is a National Phase under 35 U.S.C. 371 of International Application No. PCT/UA2008/000041 filed 11 Jul. 2008, which claims priority to Ukranian Application No. U 2007 07897 filed 12 Jul. 2007. The entire text of each of the above referenced disclosures is specifically incorporated herein by reference without disclaimer.

FIELD OF THE INVENTION

The invention concerns new substances based upon fine pyrogenic silica, or AEROSIL (commercial pharmaceutical names SILARD P, SILEX, ATOXIL) that contains serrathiopeptidase immobilized thereon. Such composition is active in the lysis of necrotizing tissues, cleanses would surfaces, improves blood supply to tissues, eliminates an objectionable putrificient odour, has an anti-edematous effect.

BACKGROUND

Treatment of festering wounds with an apparent necrosis of tissues, especially wherein significant exudation is evident, presents a very complicated problem, since there are very few therapeutic compositions available to cope with the processes (1,2).

Conventional preparations that are used in the course of contaminated surgery and have quite a good antibacterial effect are not sufficiently effective in inhibiting necrosis. Where the preparations are indeed effective, they have an ointment form, feature a low sorptive capacity and would not be easily removed when dressings are replaced (ophlotrimol-P, iruxol) (3).

Moreover, they all have no antihypoxic effect, are non-durable, and therefore do not produce any stable effect in the treatment of suppurative complications in soft tissues, which complications result in considerable necrosis.

The preparation bearing closely on the invention is known as "imosgent" and comprising a xerogel of methylsilicic acid with the antibiotic gentamicin immobilized thereon (4). This preparation has a durable antimicrobic effect on pathogenic aerobic microorganisms and is effective for the treatment of burns and festering wounds. Yet this preparation is insufficiently effective in the treatment of suppurative complications in soft tissues, which complications result in necrosis of the tissues, it does not improve blood supply to the tissues, has no antihypoxic and sorptive action.

SUMMARY

According to the invention there is provided an antimicrobial composition substantially consisting of a siliceous sorbent and a medicinal agent immobilized thereon, wherein the siliceous sorbent is pyrogenic silica and the medicinal agent is serrathiopeptidase, both present in the following amounts, % by weight:

| | |
|---|---|
| pyrogenic silica | 99 to 90 |
| serrathiopeptidase | 1 to 10. |

This invention contemplates the antimicrobial composition for use as a medicament for the treatment of festering wounds, trophic ulcers and burns, infiltrations with marked necrotic and exudative components.

The invention also consists in the provision of a method for treating festering wounds, trophic ulcers and burns, infiltrations with marked necrotic and exudative components by applying the antimicrobial composition of the present invention topically to the surface wound.

BEST MODE FOR CARRYING OUT THE INVENTION

Such a composition was not known before.

AEROSIL is fine pyrogenic silica, that consists of hydrated globules of an average radius of 4.35 nm, aerogel of polisilicic acid $SiO2*\times H2O$, the water content being up to 10% by weight. Pyrogenic silica may be used orally as enterosorbent and as a matrix for immobilizing medical products.

The composition of the invention hereinafter referred to as Sertasil is obtained in the following way.

The Method of Obtaining Sertasil

The method of obtaining consists in the formation of a solution or a suspension of serrathiopeptidase in a proper solvent in a predetermined proportion, that is added to a solid adsorbent (pyrogenic silica, polimethylsiloxane and so on) by means of impregnation, and subsequent lyophilic, vacuum or air drying at temperatures below 40-45° C. until obtaining a light air-dry white powder or as a result of mechanical dispersion of an active substance on the adsorbent surface.

EXAMPLES OF PREPARING SERTASIL ARE SET FORTH BELOW

Example 1

100 mg of serrathiopeptidase are dissolved in 100 ml of distilled water and stirred for 30 to 60 minutes at room temperature. Then AEROSIL A-300 in the amount of 10 g is added into the solution while stirring is continued. The mixture thus obtained is dried in vacuum at a temperature of 30° C. A granular white powder is formed.

Example 2

16 mg of serrathiopeptidase are dissolved in 10 ml of distilled water and stirred for 30 to 60 minutes at room temperature. Then 1 g of AEROSIL A-300 (ATOXIL) is added into the solution while the stirring is continued. The mixture thus obtained is dried in vacuum at a temperature of 40° C. A granular white powder is formed.

The preparation is used for the treatment of festering wounds, third-degree and fourth-degree burns, trophic ulcers of various etiology where necrosis of the tissues usually occurs. It eliminates odour, removes pus and necrotic tissues from wounds.

It was found that only solutions of serrathiopeptidase containing no more than 0.5% of active substance should be taken for obtaining the preparation Sertasil for use in the treatment of third-degree and fourth-degree burns, deep wounds, trophic ulcers with marked necrotic and exudative components.

Sertasil was used in the treatment of 47 patients that had deep trophic ulcers, third-degree burns, gangrenes complicated with arteriosclerosis obliterans of low extremities, festering wounds in the exudation stage with marked dense necroses on their surface, which could not be removed by other methods (including operative intervention), inflammatory infiltrations (resulting from a bullet wound).

Methods for Treating Wounds

Example 1: Patient B, born 1948, was hospitalized with a diagnosis of thermal burns of the right thigh and shank, 4%, HI B-degree. The state of the patient was moderate, the body temperature was 38.5° C., the whole surface of the skin and subcutaneous basis in the affected area was necrotized with a dense scab. The operative intervention, namely necrectomy, was performed. Sertasil was applied to the wound surface. After 2 hours, the temperature decreased. A complete wound cleansing from necrotic masses took place over 48 hours. Among the preparations of systemic action the patient obtained only anaesthetics and vascular agents (in view of allergic reaction on antibiotics of the most commonly used groups). Henceforth bandages were done with using methyluracilic ointment every 48 hours until complete healing. The wounds healed completely over 17 days.

Example 2: Patient M., born 1964, was admitted to a surgical department with a diagnosis of a bullet wound complicated with inflammatory infiltration of the anterior abdominal wall. On the examination an infiltration 11.0×6.5 cm in the left iliac area was found. In the infiltration centre there was a bullet hole 1.5×0.7 cm with a wound channel located from the outside inside, about 3.5 cm long. Tissues around the wound channel were necrotized, puffed up, dark. At the bottom of the wound channel a bullet was found. The patient on coming in was operated—the bullet was removed, necrectomy was performed. In the postoperative period, he took following medicines: cephtriaxon 1.0 g twice daily, intramuscularly, for 5 days, diclofenac sodium 3.0 ml intramuscularly, once daily for 3 days, lidase 64 units once daily, intramuscularly, UHF on the infiltration area during 7 days, daily bandaging with ioddycerin, dioxysole. The performed treatment had no substantial effect: the infiltration kept up previous sizes, no evidence of the wound cleansing and healing was observed. The patient rejected outright the proposed surgical treatment—excising the infiltration. It was decided to cure using the preparation SertaSil by means of administering it in the wound channel after pretreatments with solution of 3% hydrogen peroxide. During next 48 hours, the wound channel was completely cleansed from necrotic masses, over 7-8 days since the treatment began, the infiltration became 3.0×2.5 cm, the wound channel got superficial, the wound was filled up with granulations and was actively epithelizing. The wound healed over completely and the infiltration resolved over 14 days since the beginning of treatment with the preparation SertaSil. The patient was inspected in a month—a surface scar about 1.0×0.4 cm was found in the area of the former wound infiltration. The patient made no complaints.

Example 3: Patient K., born 1935, was hospitalized with a diagnosis of chronic venous insufficiency of lower extremities, complicated with trophic ulcer, covered here and there with necrotic tissues. B. Fragilis, $E.$ $Coli$ $10^8$ in 1 g of the tissue sample was found on the microbiological examination. After two consecutive dressings with SertaSil, no microbes were detected, the ulcer was completely cleansed in 3 days. Henceforth methyluracilic ointment was used for bandages until the complete healing that occurred in 17 days.

In view of the foregoing, the new preparation SertaSil may be used for local treatment of wounds of various genesis, trophic ulcers, abscesses, infiltrations, burns, etc., with a pronounced necrotic component that cannot be removed by other methods (including an operative one), for various reasons.

LITERATURE

1. Afinogenov G. E., Elinov I. P., Antiseptics in surgery.—L.: Medizina, 1987.—144 pp.
2. Blatun L. A., Yakovlev V. P. Modem aspects of general and local antibacterial therapy of anaerobic infection of soft tissues//Thes. Rep. All-Union sympos. "Anaerobic non-clostridial infection in contaminated surgery".-Ternopol, 1989.-pp. 6-8.
3. Mashkovsky M. D. Drugs.—Kharkov: Publishing House Torsin, 1997.—Band 1, p. 268.
4. Znamensky V. A., Vosianov A. F., Vosianova Zh. M. et al. Use of treatment preventatives, based on organosilicon sorbents//Procedure recommendations.—Kiev, 1994.—14 pp.

We claim:

1. A method for treating a wound, comprising the steps:
    a) providing an effective amount of a composition of matter comprising a dry powder antimicrobial composition comprising from 90 to 99% by weight a silicious absorbent made of:
        globules of hydrated pyrogenic silica and polysilicic acid ($SiO_2*H_2O$); and
        the remainder by weight, comprising 1% to 10% serrathiopeptidase immobilized thereon; and
    b) applying said composition to the surface of said wound.
2. The method of claim 1, said pyrogenic silica having an average radius of 4.35 nm.
3. The method of claim 1, said wound selected from the group consisting of a festering wound, a necrotic wound, an exudative wound, and a wound with inflammatory infiltration.

* * * * *